United States Patent
Magna et al.

(10) Patent No.: US 9,499,455 B2
(45) Date of Patent: Nov. 22, 2016

(54) PROCESS FOR THE SELECTIVE DIMERISATION OF ETHYLENE TO 1-BUTENE

(71) Applicant: IFP Energies nouvelles, Rueil-Malmaison (FR)

(72) Inventors: Lionel Magna, Lyons (FR); Helene Olivier-Bourbigou, Saint Genis-Laval (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/790,734

(22) Filed: Jul. 2, 2015

(65) Prior Publication Data

US 2016/0002123 A1   Jan. 7, 2016

(30) Foreign Application Priority Data

Jul. 4, 2014   (FR) ...................... 14 56470

(51) Int. Cl.
| | |
|---|---|
| *C07C 2/24* | (2006.01) |
| *C08F 110/02* | (2006.01) |
| *C07C 2/30* | (2006.01) |
| *B01J 31/14* | (2006.01) |
| *B01J 31/02* | (2006.01) |

(52) U.S. Cl.
CPC .............. *C07C 2/30* (2013.01); *B01J 31/0204* (2013.01); *B01J 31/0212* (2013.01); *B01J 31/143* (2013.01); *B01J 2231/32* (2013.01); *B01J 2531/002* (2013.01); *B01J 2531/31* (2013.01); *B01J 2531/46* (2013.01); *C07C 2531/02* (2013.01); *C07C 2531/14* (2013.01)

(58) Field of Classification Search
CPC   B01J 31/0214; B01J 31/143; B01J 31/0212; B01J 2231/32; B01J 2531/46; B01J 2531/31; B01J 2531/002; C07C 2/30; C07C 11/08; C07C 2531/14; C07C 2531/02
USPC .......................................... 585/512; 526/352
See application file for complete search history.

(56) References Cited

U.S. PATENT DOCUMENTS 3,879,485 A    4/1975   Belov et al.
6,121,502 A *  9/2000   Tembe ..................... C07C 2/30
                                                  585/511

FOREIGN PATENT DOCUMENTS

| EP | 0516852 A1 | 12/1992 |
|---|---|---|
| EP | 0722922 A1 | 7/1996 |
| GB | 853229 | * 11/1960 |

OTHER PUBLICATIONS

French Search Report for FR-1456470 dated Mar. 5, 2015.
English Abstract of EP0516852, Publication Date: Dec. 9, 1992.

* cited by examiner

*Primary Examiner* — William Cheung
(74) *Attorney, Agent, or Firm* — Millen, White, Zelano, Branigan, P.C.

(57) ABSTRACT

The invention concerns a process for the selective dimerization of ethylene to 1-butene employing a catalytic composition comprising at least one alkoxy or aryloxy titanium compound, at least one additive selected from ether type compounds and at least one aluminium compound.

21 Claims, No Drawings

PROCESS FOR THE SELECTIVE DIMERISATION OF ETHYLENE TO 1-BUTENE

The present invention relates to the selective dimerization of ethylene to 1-butene. One aim of the invention is to provide a process for the dimerization of ethylene using a particular catalytic composition.

PRIOR ART

Among the catalytic systems which are capable of selectively dimerizing ethylene to 1-butene, it is possible to identify in the literature catalytic systems based on vanadium (S. Zhang et al. *Organometallics* 2009, 28, 5925; K. Nomura et al. *Inorg. Chem.* 2013, 52, 2607), iron or cobalt (S. Song et al. *J. Organomet. Chem.,* 2011, 696, 2594; V. Appukuttan et al. *Organometallics* 2011, 30, 2285), tungsten (H. Olivier et al. *J. Mol. Catal. A: Chem.* 1999, 148, 43; R. Tooze et al. Sasol Technology WO2005089940A2, 2005), tantalum (S. McLain et al. *J. Am. Chem. Soc.,* 1978, 100(4), 1315; R. Schrock et al. *Pure & App. Chem.,* 1980, 52, 729), nickel (S. Mukherjee et al. *Organometallics* 2009, 28, 3074; K. Wang et al. *Catal. Commun.* 2009, 10, 1730; H. Liu et al. *Dalton Trans.* 2011, 40, 2614; J. Flapper et al. *Organometallics* 2009, 28, 3272, K. Song et al. *Eur. J. Inorg. Chem.* 2009, 3016) or indeed Ti (A. W. Al-Sa'doun, *Applied Catalysis A: General,* 1993, 105, 1-40).

Of these systems, those based on titanium are by far the best. In the patent U.S. Pat. No. 2,943,125, K. Ziegler described a method for the dimerization of ethylene to 1-butene using a catalyst obtained by mixing trialkylaluminium and a titanium or zirconium tetraalcoholate. During the reaction, a certain quantity of high molecular mass polyethylene is also formed; this has a considerable deleterious effect on the implementation of the process.

Several improvements have been proposed in order to reduce the quantity of polyethylene, in particular in the patent U.S. Pat. No. 3,686,350, which recommends the use of organic phosphorus compounds jointly with the elements of the catalyst, in the patent U.S. Pat. No. 4,101,600, which describes treating a catalyst with hydrogen, or in the patent U.S. Pat. No. 3,879,485, which describes the use of various ethers as solvents for the reaction medium. Although these modifications to the initial catalytic system improve the selectivity of the reaction, they turn out to be of little practical use, in particular in an industrial process in which the 1-butene has to be separated from the solvent leaving only traces of polar compound in the butenes.

From this point of view, the Applicant's patent FR 2 552 079 has demonstrated that using a catalyst obtained by the interaction of a trialkylaluminium on the one hand with a pre-formed mixture of alkyl titanate and an ether type additive in stoichiometric quantities on the other hand appreciably improves the activity and selectivity of such catalysts for the dimerization of ethylene to 1-butene. Patent FR 2 552 079 also teaches that the use of said ether type additives in molar ratios of more than 10 with respect to the alkyl titanate slows down the reaction considerably and results in poorer selectivity.

While it is known that increasing the molar ratio between the alkyl aluminium and the alkyl titanate leads to an improvement in productivity, under the conditions of patent FR 2 552 079 this occurs to the detriment of the operability of the process because ever larger quantities of polymer are observed.

Increasing the reaction temperature also produces the same effects, in particular a reduction in the stability of the catalyst and an increase in the proportion of polymer. The principal disadvantage of catalytic systems based on titanium used for the selective formation of 1-butene is thus the formation of a non-negligible quantity of polymers. This polymer formation may be the source of rapid deactivation of the catalyst and increased difficulties with operability.

One aim of the invention is to provide a process for the selective dimerization of ethylene to 1-butene with a reduced or even near-zero production of polyethylene, and greatly improved operability.

The invention concerns a process for the selective dimerization of ethylene to 1-butene using a catalytic composition comprising at least one alkoxy or aryloxy titanium compound, at least one additive selected from ether type compounds and at least one aluminium compound, in which the molar ratio between the additive and the titanium compound is strictly more than 10 and the molar ratio between the aluminium compound and the alkoxy or aryloxy titanium compound is strictly more than 4.

It has now been found that a process using a catalytic composition comprising at least one alkoxy or aryloxy titanium compound, at least one additive selected from ether type compounds and at least one aluminium compound, in which the molar ratio between the additive and the alkoxy or aryloxy titanium compound is strictly more than 10 and the molar ratio between the aluminium compound and the alkoxy or aryloxy titanium compound is strictly more than 4 can be used to obtain a very high selectivity for the selective dimerization of ethylene to 1-butene with a reduced or even zero polyethylene production.

DETAILED DESCRIPTION OF THE INVENTION

In the remainder of the text and above, unless otherwise indicated, the molar ratio between the additive and the titanium compound will be expressed in moles of additive per mole of titanium. In the remainder of the text and above, unless otherwise indicated, the molar ratio between the aluminium compound and the alkoxy or aryloxy titanium compound will be expressed in moles of aluminium per mole of titanium.

The invention concerns a process for the selective dimerization of ethylene to 1-butene using a catalytic composition comprising at least one alkoxy or aryloxy titanium compound, at least one additive selected from ether type compounds and at least one aluminium compound, in which the molar ratio between said additive and the titanium compound is strictly more than 10 and the molar ratio between the aluminium compound and the alkoxy or aryloxy titanium compound is strictly more than 4.

Advantageously, the molar ratio between the additive and the alkoxy or aryloxy titanium compound of the catalytic composition is in the range 11 to 19.

Advantageously, the molar ratio between the aluminium compound and the alkoxy or aryloxy titanium compound of the catalytic composition is in the range 5 to 15.

The alkoxy titanium compound used in the present invention advantageously has the general formula [Ti(OR)$_4$], in which R is a linear or branched alkyl radical containing 2 to 30 carbon atoms. The radical R may comprise substituents based on a nitrogen, phosphorus, sulphur and oxygen heteroatom.

Non-limiting examples of preferred alkoxy radicals which may be cited include: tetraethoxy, tetraisopropoxy, tetra-n-butoxy, tetra-2-ethyl-hexyloxy.

The aryloxy titanium compound used in the present invention advantageously has the general formula [Ti(OR')$_4$], in which R' is an aryl radical which may or may not be substituted with alkyl, aryl or aralkyl groups containing 2 to 30 carbon atoms. The radical R' may comprise substituents based on a nitrogen, phosphorus, sulphur and oxygen heteroatom.

Non-limiting examples of preferred aryloxy radicals which may be cited include: phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-tert-butyl-6-phenyl-phenoxy, 2,4-di-tert-butyl-6-phenylphenoxy, 2,6-diisopropylphenoxy, 2,6-di-tert-butylphenoxy, 4-methyl-2,6-di-tert-butylphenoxy, 2,6-dichloro-4-tert-butylphenoxy and 2,6-dibromo-4-tert-butylphenoxy, the biphenoxy radical, binaphthoxy, 1,8-naphtalene-dioxy.

The aluminium compound of the invention is advantageously selected from the group formed by hydrocarbylaluminium compounds, tris(hydrocarbyl)aluminium compounds, chlorine-containing or bromine-containing hydrocarbylaluminium compounds and aluminoxanes.

The tris(hydrocarbyl)aluminium compounds and the chlorine-containing or bromine-containing hydrocarbylaluminium compounds are represented by the general formula AlR"$_m$Y$_{3-m}$ in which R" is a hydrocarbyl radical, preferably alkyl containing 1 to 6 carbon atoms, Y is a chlorine or bromine atom, preferably a chlorine atom, and m is a number from 1 to 3.

Preferably, the aluminium compound is selected from the group formed by dichloroethylaluminium (EtAlCl$_2$), ethylaluminium sesquichloride (Et$_3$Al$_2$Cl$_3$), chlorodiethylaluminium (Et$_2$AlCl), chlorodiisobutylaluminium (i-Bu$_2$AlCl), triethylaluminium (AlEt$_3$), tripropylaluminium (Al(n-Pr)$_3$), triisobutylaluminium (Al(i-Bu)$_3$). The preferred aluminium compound is triethylaluminium (AlEt$_3$).

The additive of the catalytic composition of the invention is advantageously selected from the group formed by diethyl ether, diisopropylether, 2-methoxy-2-methylpropane, 2-methoxy-2-methylbutane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl)ether and benzofuran, used alone or as a mixture.

A particular composition in accordance with the invention is a composition in which the titanium compound is [Ti(O"Bu)$_4$], the additive is THF and is in a molar ratio (mol/mol) with respect to the titanium compound (THF/Ti) which is strictly more than 10, preferably in the range 11 to 19, and the aluminium compound is triethylaluminium in a molar ratio (mol/mol) with respect to the titanium compound (AlEt$_3$/Ti) which is strictly more than 4, preferably in the range 5 to 15.

Process for the Preparation of the Catalytic Composition Used in the Process of the Invention The catalytic composition in accordance with the invention, i.e. the alkoxy or aryloxy titanium compound, the ether type additive and the aluminium compound, may be used as a mixture with a solvent selected from the group formed by aliphatic and cycloaliphatic hydrocarbons such as hexane, cyclohexane, heptane, butane or isobutane, by an unsaturated hydrocarbon such as a monoolefin or a diolefin containing 4 to 20 carbon atoms, for example, by an aromatic hydrocarbon such as benzene, toluene, ortho-xylene, mesitylene, or ethylbenzene, or by a chlorine-containing hydrocarbon such as chlorobenzene or dichloromethane, pure or as a mixture. Advantageously, aliphatic hydrocarbons such as cyclohexane or n-heptane, and aromatic hydrocarbons such as toluene and ortho-xylene are used.

In accordance with one embodiment of the catalytic composition of the invention, the aluminium compound is added to a solution containing the additive and the alkoxy or aryloxy titanium compound present in a molar ratio which is strictly more than 10, preferably in a ratio in the range 11 to 19, the molar ratio of the aluminium compound to the titanium compound being strictly more than 4, preferably in the range 5 to 15.

The concentration of titanium in the catalytic solution is advantageously in the range $1 \times 10^{-9}$ to 1 mol/L, preferably in the range $1 \times 10^{-6}$ to 0.5 mol/L.

The temperature at which the components of the catalytic composition are mixed is advantageously in the range −40° C. to +250° C., preferably in the range 0° C. to +150° C., for example at a temperature close to ambient temperature (15° C. to 30° C.). Mixing may be carried out under an ethylene or inert gas atmosphere.

Dimerization Reaction

The process of the invention is a process for the selective dimerization of ethylene to 1-butene using the catalytic composition described above.

The ethylene dimerization reaction is advantageously carried out under a total pressure of 0.5 to 20 MPa, preferably 0.5 to 10 MPa, and at a temperature of 20° C. to 180° C., preferably 40° C. to 140° C.

In accordance with one embodiment, the dimerization reaction is carried out in batch mode. A selected volume of catalytic composition constituted as described above is introduced, advantageously in solution, into a reactor provided with the usual stirring, heating and cooling devices, then it is pressurized using ethylene, advantageously to the desired pressure, and the temperature is adjusted, preferably to the desired value. The dimerization reactor is maintained at a constant pressure by introducing ethylene until the total volume of liquid produced represents, for example, 2 to 50 times the volume of the catalytic solution originally introduced. The catalyst is then destroyed using any of the usual means known to the skilled person, then the reaction products and the solvent are withdrawn and separated.

In accordance with another preferred embodiment, the catalytic ethylene dimerization reaction is carried out in continuous mode. In a first variation, on the one hand a solution containing the titanium compound and the additive and on the other hand a solution containing the aluminium compound are separately injected into a reactor maintained under a constant pressure of ethylene in a manner such that the catalytic composition of the invention is produced. Said reactor is stirred using conventional mechanical means known to the skilled person or by external recirculation. The temperature and pressure of the ethylene are kept constant at the desired values using conventional means known to the skilled person. The reaction mixture is withdrawn using a liquid level-regulated valve in order to keep it constant. The catalyst is continuously destroyed using any usual means known to the skilled person, then the products obtained from the reaction as well as the solvent are separated, for example by distillation. The ethylene which has not been transformed may be recycled to the reactor. The residues of catalyst included in a heavy fraction may be incinerated.

In a second variation, on the one hand a solution containing the titanium compound and the additive and on the other hand the aluminium compound are injected into a first reactor/mixer in a manner such that the catalytic composition of the invention is produced; said composition is then continuously introduced into a reactor maintained under a constant pressure of ethylene. This mixture in the first reactor/mixer may be produced under an inert atmosphere or under an ethylene atmosphere. The reaction mixture is withdrawn using a liquid level-regulated valve in order to keep it constant. The catalyst is continuously destroyed using any usual means known to the skilled person, then the products obtained from the reaction as well as the solvent are separated, for example by distillation. The ethylene which has not been transformed may be recycled to the reactor. The residues of catalyst included in a heavy fraction may be incinerated.

Products Obtained

The process of the invention can be used for the selective production of 1-butene. This compound is of use as co-monomers with ethylene in the manufacture of linear low density polyethylene.

The following examples illustrate the invention without limiting its scope.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 14/56.470, filed Jul. 4, 2014, are incorporated by reference herein.

EXAMPLES

Examples 1-4

The ethylene dimerization tests presented in Table 1 below were carried out in a stainless steel autoclave with a useful volume of 500 mL, provided with a jacket in order to regulate the temperature by oil circulation. Stirring was provided using a Rushton impeller with a mechanical drive.

40 mL of n-heptane as well as 5 mL of a 0.085 mol/L solution of titanium compound in n-heptane were introduced into this reactor under an atmosphere of ethylene and at ambient temperature. Once the temperature of the reactor had reached 53° C., the desired quantity of aluminium-based co-catalyst (already diluted in 5 mL of n-heptane) was introduced under ethylene pressure. The ethylene pressure was maintained at 23 MPa and the temperature was maintained at 53° C. After 1 h of reaction, ethylene introduction was halted and the reactor was cooled to 25° C. The reactor was then degassed through a gas meter. This gas was analysed by gas phase chromatography. The liquid phase contained in the reactor was then weighed and analysed by gas phase chromatography. The polymer produced was recovered, dried and weighed.

The composition of the products obtained is given in Table 1 below. In this table, the activity is defined as the mass of ethylene consumed per gram of titanium initially introduced per hour. The C4 distribution (% $C_4$) is the quantity of olefins containing 4 carbon atoms in the total distribution. The percentage % $C_4^{=1}$ represents the selectivity for the linear 1-butene product in the $C_4$ cut. The quantity of polymer (%PE) corresponds to the mass of polymer recovered, as a function of the total distribution.

TABLE 1

| Ex. | Ti compound | Additive | "Additive/Ti" molar ratio | "Al" co-catalyst | Al/Ti molar ratio | T (° C.) | t (min) | Activity (g/gTi/h) | % $C_4$ (% $C_4^{=1}$) | % PE |
|---|---|---|---|---|---|---|---|---|---|---|
| 1 | [Ti(O"Bu)$_4$] | THF | 4 | AlEt$_3$ | 3.0 | 53 | 87 | 6200 | 94 (99$^+$) | 0.05 |
| 2 | [Ti(O"Bu)$_4$] | THF | 4 | AlEt$_3$ | 6.8 | 53 | 62 | 12400 | 94 (99$^+$) | 0.30 |
| 3 | [Ti(O"Bu)$_4$] | THF | 10.7 | AlEt$_3$ | 6.8 | 53 | 114 | 6800 | 94 (99$^+$) | nd* |
| 4 | [Ti(O"Bu)$_4$] | THF | 18.8 | AlEt$_3$ | 6.9 | 53 | 125 | 7500 | 95 (99$^+$) | nd* |

*nd = not detected (this designation characterizes the complete absence of polymer)

In this table, Examples 1 and 2 show that in the compositions with a molar ratio THF/Ti <10 (comparative examples, not in accordance with the invention), increasing the molar ratio AlEt$_3$/Ti from 3 to 6.8 results in a considerable increase in the production of polyethylene.

Examples 3 and 4, in accordance with the invention, demonstrate that the compositions with a THF/Ti molar ratio strictly greater than 10, with a AlEt$_3$/Ti ratio of 6.8 (compare with Example 2), have very good activity and selectivity for the selective dimerization of ethylene to 1-butene and without the production of polyethylene.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the selective dimerization of ethylene to 1-butene, said process comprising selectively dimerizing ethylene in the presence of a catalytic composition comprising at least one alkoxy or aryloxy titanium compound, at least one ether compound, and at least one aluminum compound, in which the molar ratio between the ether compound and the alkoxy or aryloxy titanium compound is more than 10 and the molar ratio between the aluminum compound and the alkoxy or aryloxy titanium compound is more than 4.

2. The process according to claim 1, in which the molar ratio between the ether compound and the alkoxy or aryloxy titanium compound of the catalytic composition is in the range of 11 to 19.

3. The process according to claim 1, in which the molar ratio between the aluminum compound and the alkoxy or aryloxy titanium compound of the catalytic composition is in the range of 5 to 15.

4. The process according to claim 1, in which the alkoxy titanium compound is of the formula [Ti(OR)$_4$], in which R is a linear or branched alkyl radical containing 2 to 30 carbon atoms.

5. The process according to claim 1, in which the aryloxy titanium compound is of the formula [Ti(OR')$_4$], in which R' is an aryl radical which is unsubstituted or is substituted with alkyl, aryl or aralkyl groups containing 2 to 30 carbon atoms.

6. The process according to claim 1, in which the aluminum compound is selected from hydrocarbylaluminum compounds, tris(hydrocarbyl)aluminum compounds, chlorine-containing or bromine-containing hydrocarbylaluminum compounds, and aluminoxanes.

7. The process according to claim 6, in which the aluminum compound is selected from dichloroethylaluminum, ethylaluminum sesquichloride, chlorodiethylaluminum, chlorodiisobutylaluminum, triethylaluminum, tripropylaluminum, and triisobutylaluminum.

8. The process according to claim 1, wherein the titanium compound is [Ti(O"Bu)$_4$], the ether compound is tetrahydrofuran and is in a molar ratio with respect to the titanium compound which is more than 10, and the aluminum compound is triethylaluminum in a molar ratio with respect to the titanium compound which is more than 4.

9. The process according to claim 1, in which the tetrahydrofuran is selected from diethyl ether, diisopropylether, 2-methoxy-2-methylpropane, 2-methoxy-2-methylbutane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether, and benzofuran, used alone or in mixture.

10. The process according to claim 1, in which the catalytic composition is used as a mixture with a solvent selected from aliphatic hydrocarbons, cycloaliphatic hydrocarbons, unsaturated hydrocarbons containing 4 to 20 carbon atoms, and chlorine-containing hydrocarbon, alone or in mixture.

11. The process according to claim 1, wherein the dimerization reaction is performed under a total pressure of 0.5 to 20 MPa and at a temperature of 20° C. to 180° C.

12. The process according to claim 1, carried out in a batch mode.

13. The process according to claim 1, in which a selected volume of the catalytic composition is introduced into a reactor provided with stirring, heating and cooling means, the reactor is then pressurized using ethylene, and the temperature is adjusted.

14. The process for the selective dimerization of ethylene to 1-butene according to claim 1, wherein a solution containing the titanium compound and the ether compound and a solution containing the aluminum compound are introduced separately into a reactor maintained under a constant pressure of ethylene in a manner so as to produce the catalytic composition.

15. The process for the selective dimerization of ethylene to 1-butene according to claim 1, wherein a solution containing the titanium compound and the ether compound and a solution containing the aluminum compound are introduced into a first reactor/mixer in a manner so as to produce the catalytic composition, said composition then being continuously introduced into a reactor maintained under a constant pressure of ethylene.

16. A process for the preparation of a catalytic composition comprising at least one alkoxy or aryloxy titanium compound, at least one ether compound, and at least one aluminum compound, said process comprising; adding the aluminum compound to a solution containing the ether compound and the alkoxy or aryloxy titanium compound present in a molar ratio of more than 10, and the molar ratio of the aluminum compound to the titanium compound is more than 4.

17. The process according to claim 1, carried out in a continuous implementational mode.

18. The process according to claim 2, in which the molar ratio between the aluminum compound and the alkoxy or aryloxy titanium compound of the catalytic composition is in the range of 5 to 15.

19. The process according to claim 1, wherein the alkoxy and aryloxy groups of said at least one alkoxy or aryloxy titanium compound are selected from tetraethoxy, tetraisopropoxy, tetra-n-butoxy, tetra-2-ethyl-hexyloxy, phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-tert-butyl-6-phenylphenoxy, 2,4-di-tert-butyl-6-phenylphenoxy, 2,6-diisopropylphenoxy, 2,6-di-tert-butylphenoxy, 4-methyl-2,6-di-tert-butylphenoxy, 2,6-dichloro-4-tert-butylphenoxy and 2,6-dibromo-4-tert-butylphenoxy, binaphthoxy, and 1,8-naphtalene-dioxy.

20. The process according to claim 1, in which the catalytic composition is used as a mixture with a solvent selected from hexane, cyclohexane, heptane, butane or isobutane, a monoolefin containing 4 to 20 carbon atoms, a diolefin containing 4 to 20 carbon atoms, benzene, toluene, ortho-xylene, mesitylene, ethylbenzene, chlorobenzene and dichloromethane, alone or in mixture.

21. The process according to claim 1, wherein the dimerization reaction is performed under a total pressure of 0.5 to 10 MPa and at a temperature of 40° C. to 140° C.

* * * * *